United States Patent
Schwartz et al.

(10) Patent No.: US 10,779,740 B1
(45) Date of Patent: Sep. 22, 2020

(54) SYSTEM AND METHOD TO ENHANCE SELF-RECOVERY OF NERVE-MUSCLE DAMAGE

(71) Applicant: Center for Quantitative Cytometry, San Juan, PR (US)

(72) Inventors: Abraham Schwartz, San Juan, PR (US); Walter R. Frontera, San Juan, PR (US)

(73) Assignee: Center for Quantitative Cytometry, San Juan, PR (US)

( * ) Notice: Subject to any disclaimer, the term of this patent is extended or adjusted under 35 U.S.C. 154(b) by 0 days.

(21) Appl. No.: 16/804,378

(22) Filed: Feb. 28, 2020

(51) Int. Cl.
*A61B 5/00* (2006.01)
*A61B 5/04* (2006.01)
(Continued)

(52) U.S. Cl.
CPC ........ *A61B 5/04012* (2013.01); *A61B 5/0488* (2013.01); *A61B 5/4848* (2013.01);
(Continued)

(58) Field of Classification Search
CPC ... A61B 5/6811; A61B 5/0488; A61B 5/4888; A61B 5/4851; A61H 2230/60; A61F 2/72
See application file for complete search history.

(56) References Cited

U.S. PATENT DOCUMENTS

| 3,735,425 A | 5/1973 | Hoshall et al. |
| 3,942,516 A | 3/1976 | Glynn et al. |

(Continued)

FOREIGN PATENT DOCUMENTS

| CN | 105190578 A | 12/2015 |
| CN | 05943206 A | 9/2016 |
| CN | 206869888 U | 1/2018 |

OTHER PUBLICATIONS

Reaz et al, Techniques of EMG signal analysis: detection, processing, classification and applications, Biol. Proced. Online 2006; 8(1): 11-35.

(Continued)

*Primary Examiner* — Samchuan C Yao
*Assistant Examiner* — Matthew Standard
(74) *Attorney, Agent, or Firm* — Hoglund & Pamias, PSC; Roberto J. Rios

(57) ABSTRACT

The invention provides a retraining system that requires EM sensors, programmable computers and mechanical structures that are controlled by the programmable computers so that injured body parts of injury subjects are moved by the mechanical structures. The retraining methodology proposes the use of electromyograph (EMG) signals from a healthy subject having a healthy body part to control the mechanical structures that are coupled to the injured body parts of injury subjects. As part of the retraining system, the EMG signals of the same injured subject are also sensed by an EM sensor coupled to said injured subject in order to move the mechanical structures coupled to the injured subject. The system is calibrated to store in the programmable computers specific motions associated to the EMG signals of the healthy subject and to ensure that the EMG signals of the healthy subject and the EMG signals of the injured subject are significantly matched. Also, the system provides that the EMG signals of a single healthy subject can be used to control the movement of a plurality of mechanical structures coupled to a plurality of injured subjects to offer a group therapy session.

20 Claims, 7 Drawing Sheets

(51) Int. Cl.
*A61H 1/02* (2006.01)
*A61B 5/0488* (2006.01)

(52) U.S. Cl.
CPC .............. *A61H 1/02* (2013.01); *A61H 1/0274* (2013.01); *A61B 2505/09* (2013.01); *A61H 2201/5097* (2013.01); *A61H 2230/605* (2013.01)

(56) References Cited

U.S. PATENT DOCUMENTS

| | | |
|---|---|---|
| 4,158,196 A | 6/1979 | Crawford, Jr. |
| 2004/0267331 A1* | 12/2004 | Koeneman ......... A61N 1/36003 607/49 |

OTHER PUBLICATIONS

Visconti et al., Technical Features and Functionalities of Myo Armband: An Overview on Related Literature and Advanced Applications of Myoelectric Armbands Mainly Focused on Arm Prostheses, International Journal on Smart Sensing and Intelligent Systems, Issue 0 | vol. 0; 1-25.

\* cited by examiner

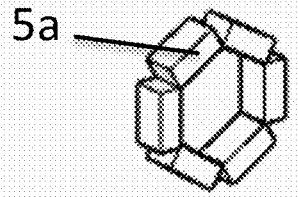
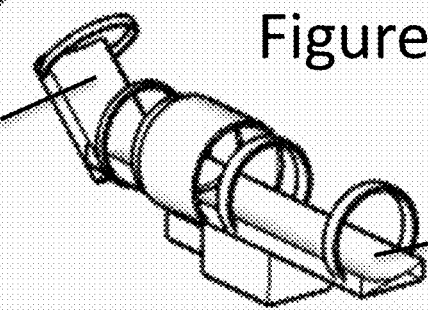
Figure 6b
Neutral position
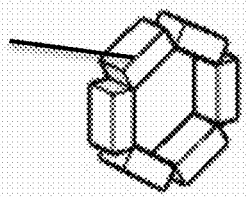
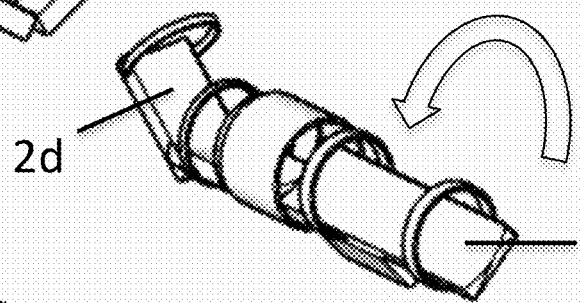
Figure 6c
Clockwise
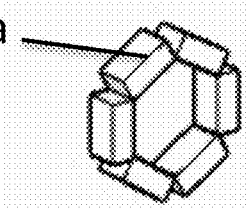
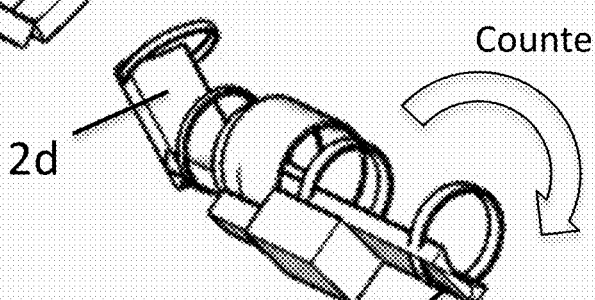
Counterclockwise
Figure 6d

SYSTEM AND METHOD TO ENHANCE SELF-RECOVERY OF NERVE-MUSCLE DAMAGE

TECHNICAL FIELD

The present system, devices and method generally relate to a therapeutic system and method that detects and uses neural impulses to move elements of an apparatus attached distal to the injury to enhance retraining sections of the body that have been rendered immobile due to injury.

BACKGROUND OF THE INVENTION

The voluntary control of muscles consists of a series of complex nerve impulses that pass from the brain through specific pathways of the nervous system to the muscle groups to move the desired portion of the body. For example, to move the fourth and fifth fingers, neural impulses travel from the brain through the ulnar nerve to the specific muscle groups to move the specific fingers via electromyo (EM) impulses. However, if a traumatic injury to this relatively unprotected nerve pathway occurs and the nerve connection to the muscle group is damaged, then the EM signals can be blocked at the site of the injury.

Through natural regeneration or neurosurgery, neural pathways can be restored, and desired motions recovered. However, to function normally, the body needs to regain the functionality across the complete neural pathway from the brain to the target muscle group. Presently, retraining is accomplished by repetitive manipulation of the desired motion by a mechanical device or by a physical therapist in hopes that the repetitive motion will stimulate reconnection of the desired neural pathway. This approach is, at best, indirect and does not take advantage of the EM signals still being generated by the nervous system that reach locations proximal to the traumatic injury.

The application of EM impulses is based on two assumptions: 1) the muscle group necessary to generate a specific motion is the same across different subjects and 2) the set of EM impulses intended to move the same muscle groups of different subjects is significantly equivalent. These assumptions have been validated and used in EM sensing systems that have the ability to control electrical and mechanical devices by Thalmic Labs® with the Myo Gesture Control Armband and CTRL-Labs™ with the CTRL-kit, as well as to control a subject's arm with another person's brain.

SUMMARY OF THE INVENTION

The present invention is a method of therapy to enhance retraining of mobility where the normal EM impulses proximal to the injury are intact and can be detected. A programmed computer reads these EM signals to control a mechanical apparatus attached to the body parts distal to the injury that needs retraining.

The methodology according to an aspect of the invention requires EM sensors, a programmable computer and a mechanical structure controlled by the computer such that the body parts distal to the injury will be moved in a desired manner. This retraining methodology also requires the participation of a normal healthy subject and the injured subject.

The EM signals from the injured subject are first evaluated to determine the location where the EM signals proximal to the injury are best detected and evaluated as to how well they correlate to EM signals from a healthy subject taken from the same location of the injured subject. Acceptable EM signal correlation enables the injured subject to use the EM signals from a healthy subject to remotely control the mechanical apparatus placed on the injured subject. The motions of the injured and healthy subjects are evaluated for consistency. This step ensures that normal motion of the injured subject can be obtained by using EM signals from a healthy subject. In addition, if the healthy subject is the therapist, the retraining procedure can be carefully controlled, as well as, provide the injured subject visual and muscle feedback while both subjects' movements are synchronized. The injured subject's own EM signals obtained proximal to the injury can then be tested to control the apparatus placed on the injured subject distal to the injury.

BRIEF DESCRIPTION OF THE DRAWINGS

Further features and advantages of the invention will become apparent from the following detailed description taken in conjunction with the accompanying figures showing illustrative embodiments of the invention, in which:

FIG. 6b shows an embodiment of the therapeutic system for the rotation of an arm in the neutral position, according to the invention.

FIG. 6c shows an embodiment of the therapeutic system for the rotation of an arm in the clockwise position, according to the invention.

FIG. 6d shows an embodiment of the therapeutic system for the rotation of an arm in the counterclockwise position, according to the invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

The System

Figure 2:
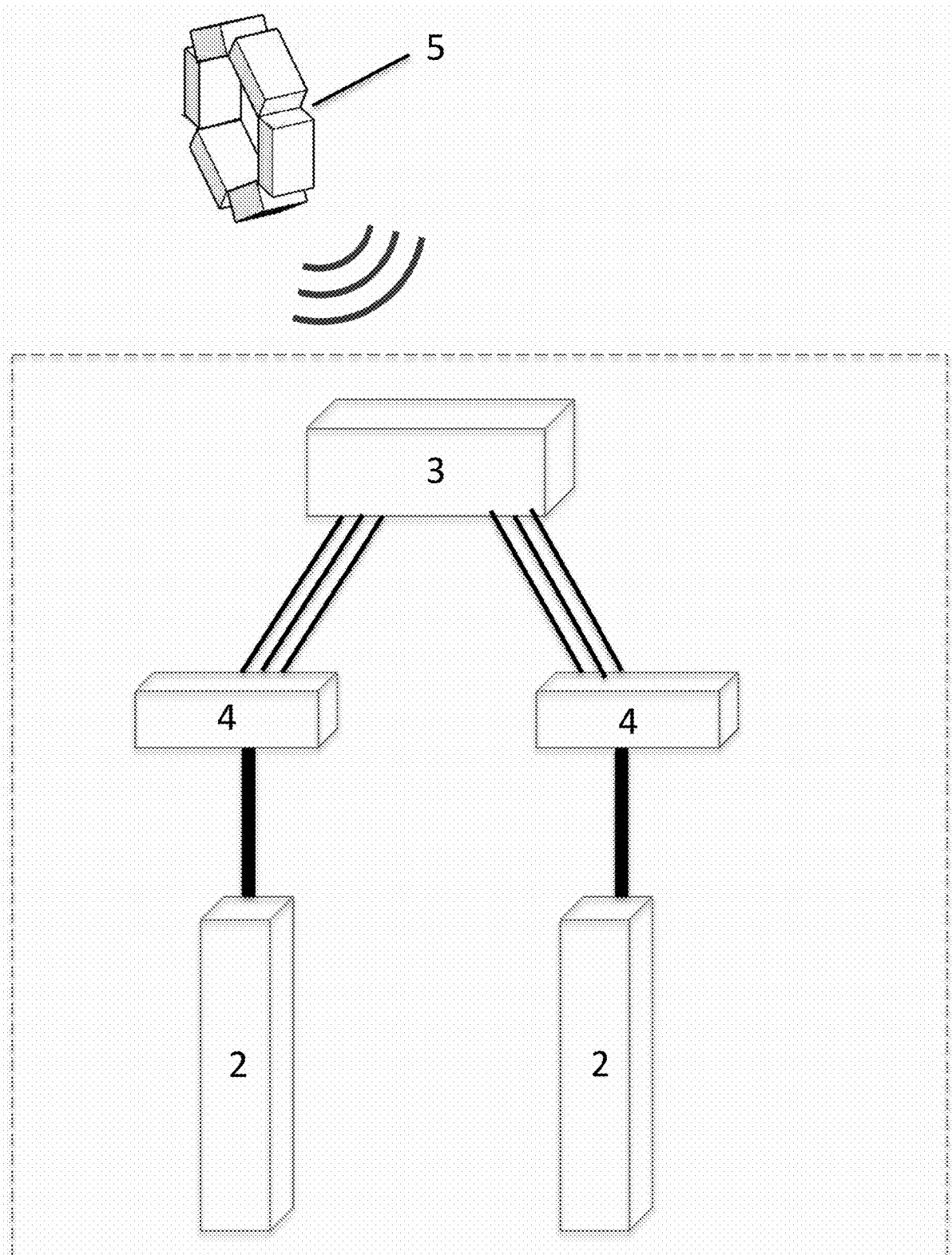
FIG. 2 illustrates the elements of the retraining system, according to the invention.
Figure 3:
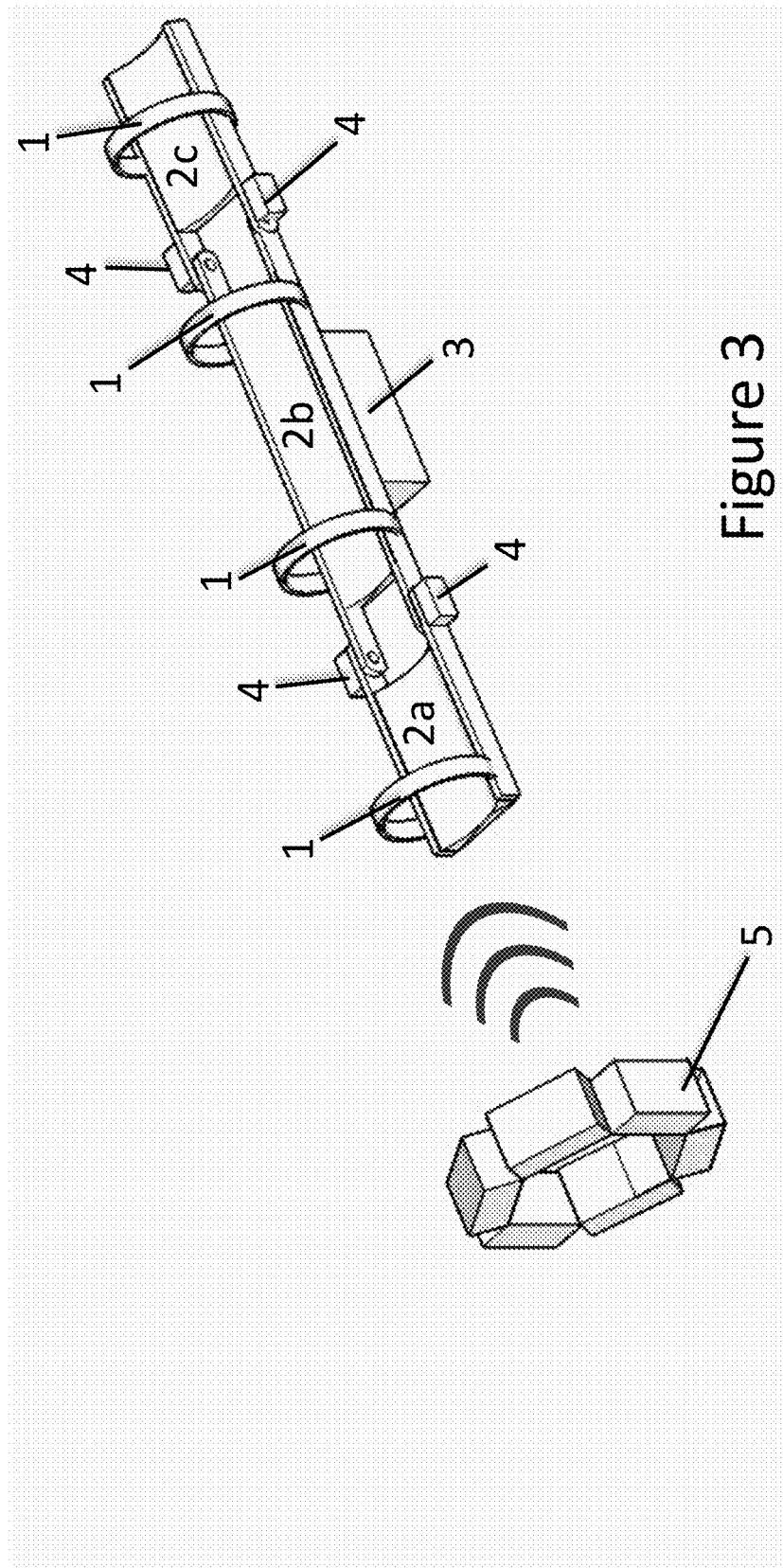
FIG. 3 shows an embodiment of the therapeutic system for the elbow and wrist, according to the invention.

The retraining system according to the invention includes EM sensors 5 placed proximal to the injury for detecting multiple EM signals that control muscle movement. The sensors 5 are connected to a processing module or microcomputer 3 and support elements (2a-2c) are attached to the body parts that are distal to the myo-neural injury. In addition, a set of mechanical servo motors (4) are mechanically connected to the support elements to move the elements along with the body parts connected thereto. It is to be understood that any mechanical connection can be used between the motor and the support elements as long as the rotation generated by the motor produce a corresponding movement (linear, rotation, bend, 2D and 3D movements, etc. . . . ) on the support elements. A graphical representation of the electrical/mechanical and signal connections between the components of the retraining system is illustrated in FIG. 2. FIG. 3 illustrates an example of the system according to an embodiment of the present invention.

In describing this invention, the components (i.e., the EM sensors and the apparatus) are referred to as the retraining system. The EM sensors worn proximal to the injury are considered the sensor devices and the components worn distal to the injury are considered the apparatus.

The EM impulses from the muscle groups are detected by a band having a plurality of sensors (5) that are distributed around the circumference of the injured limb. According to a preferred embodiment, the Myo armband from Thalmic Labs® can be used. The EM sensors 5a are connected to a processing module or microcomputer 3 that can be for example a Raspberry Pie, an Arduino Uno or any other device that contains at least one of: a processing unit, a memory and storage unit, at least one input and output unit, a video/graphics unit, and removable media.

In a preferred embodiment, the connection between the EM sensors 5a and the microcomputer 3 is performed wirelessly using any well-known wireless protocol such as but not limited to: Bluetooth, Bluetooth Low Energy (BLE), ZigBee, Z-Wave, 6LoWPAN, Thread, 2G, 3G, 4G, LTE, NB-IoT, 5G, NFC, RFID, SigFox, LoRaWAN, Ingenu, Weightless-N/P/W, ANT(+), DigiMesh, MiWi, EnOcean, Dash7, WirelessHART, WIFI and infrared. The microcomputer 3 (which can be powered by a battery or via a power outlet), in turn, is connected to one or more servo motors 4 that selectively control each joint/segment (2a-2c) of the support elements such that they can perform the desired motion(s).

Normally, when any person uses an EM system to perform a specific task, the first requirement is to calibrate a library of programmed tasks or motions that are already contained within a computer memory with the EM signals from a subject. This calibration is performed by the subject making a specific motion contained in the library of motions and allowing the computer to calibrate the subject's EM signals to the programmed motion. To ensure that the calibration is accurate, the motion of the subject needs to be visually verified. However, such verification is impossible when an injured subject has lost the ability to make such a movement.

However, the present invention provides a method where the calibration can be accomplished by comparison and adjustment of the EMGs from healthy and injured subjects via statistical analysis and A.I. network learning algorithms. These adjustments can be validated using the methodology described in the present invention.

The computer 3 is calibrated by placing the EM sensors 5a on a healthy subject that has full and normal control of the desired motions. This calibration step is the basis for the assumption that the muscle group necessary so that a limb or body part performs a specific motion is common for most normal subjects and the associated EM impulses have a significant statistical similarity to one another. The computer 3 can be used in a calibration mode where the healthy subject while wearing the EM sensors 5a performs the desired motion or motions and the sensors detect the set of EM impulses from the muscles of the healthy subject which are recorded by the microcomputer 3. This step is performed so that the set of recorded EM impulses is associated to motions of a limb or body part that are either previously stored on the library of programmed motions or new motions that are added to the library of programmed motions.

Figure 4:
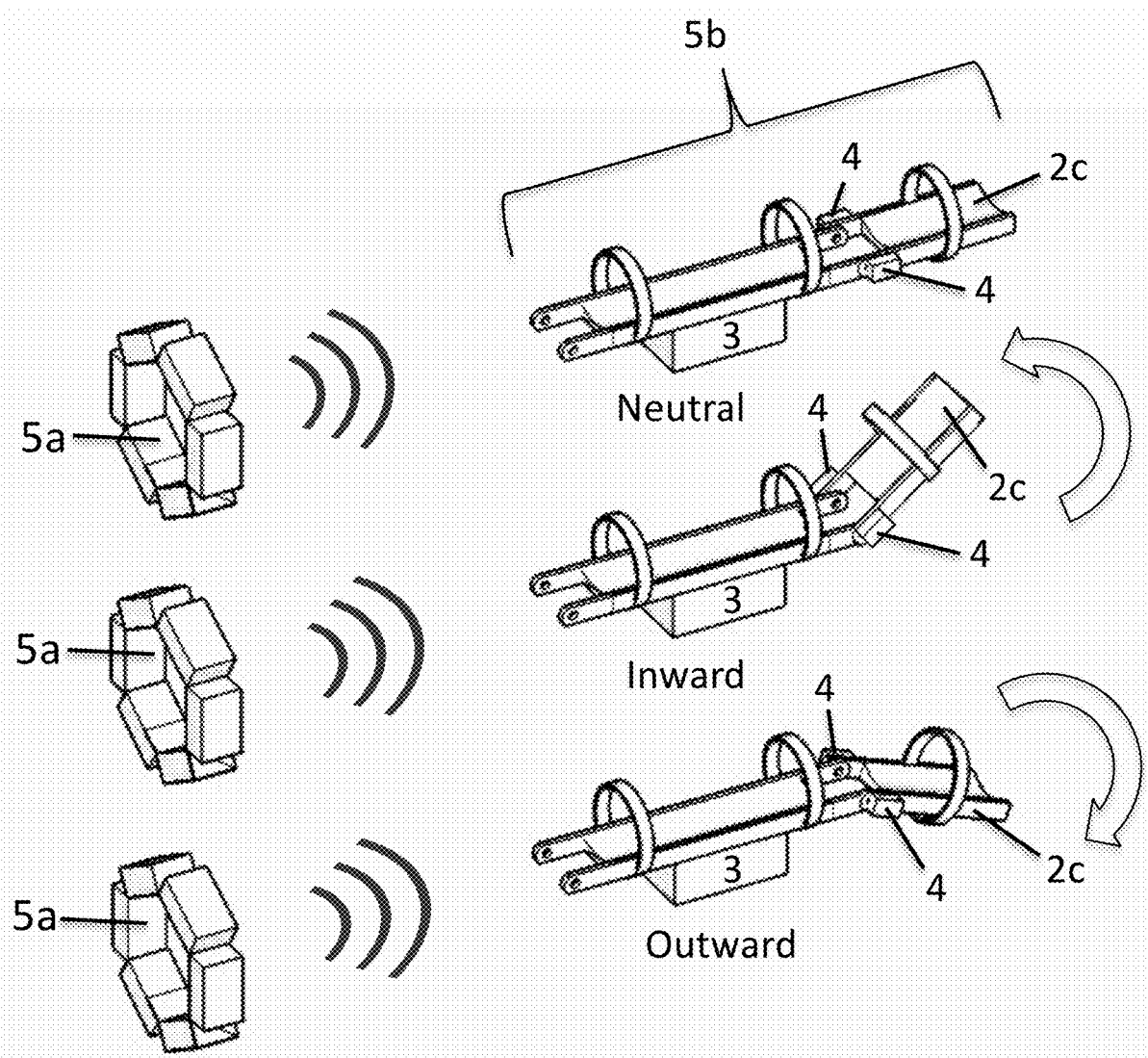
FIG. 4 shows an embodiment of the therapeutic system for a wrist with a hand in the neutral, inward and outward hand positions, according to the invention.

Once the computer is calibrated, it will selectively control the servo motors individually and in combination so that the support elements move the limb or body part to recreate different programmed motions that are associated with recorded EM impulses. Specifically, every programmed motion will correspond to specific parameters that will selectively control the operation of the servo motors 4 provided on the apparatus 5b, such parameters include but are not limited to: current, voltage, polarity, revolutions per minute (rpm), activation time and angle of rotation. For example, a programmed inward motion of a hand might activate servo motors 4 to rotate or move an angular distance of 90 degrees, in a counterclockwise direction, at a speed of 5 rpm and for a duration 3 seconds so that the support element 2c is moved as illustrated in FIG. 4. Since the apparatus 5b is coupled to the injured subject's arm, this controlled movement will also move the injured subject's hand in an inward direction. It is also envisioned that these parameters can be modified and/or updated even after being initially programmed in order to ensure that the support elements are moved in a safe manner that will prevent injuries to the limb or body part being moved. As can be appreciated, theses parameters can be selectively controlled in one servo motor or in a plurality of servo motors at the same time, one at a time, sequentially, alternating, at random or in any other combination according to limb or body part being moved.

The injured subject, while wearing the EM sensors Sa proximal to the injured limb or body part, attempts to perform the same motion or motions as the healthy subject did while the computer 3 records those EM impulses. A comparison of these two sets of recorded EM data with diagnostic software will indicate if the match is statistically significant for acceptable use of the apparatus 5b by the injured subject. This statistical comparison can be difficult since raw EMG signals are complex, non-stationary and fast transit. However, pattern recognition algorithms help in making this determination.

Figure 1A:
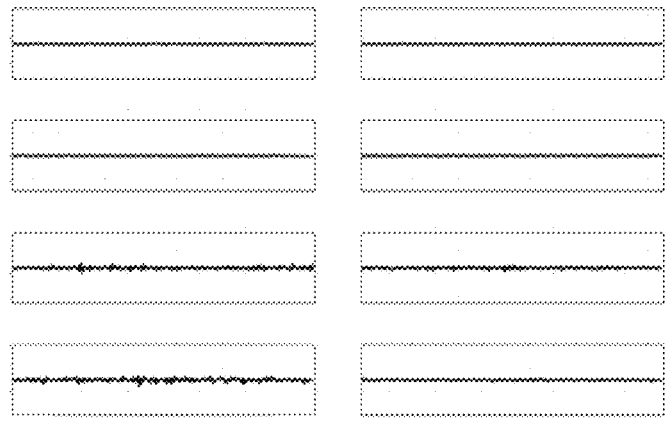
FIGS. 1a-1c show histograms of electromyo impulses from sensors in an armband for different hand movements.
Figure 1B:
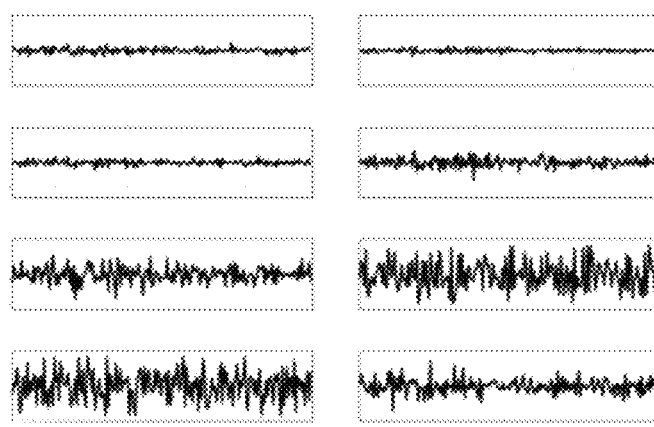
Figure 1C:
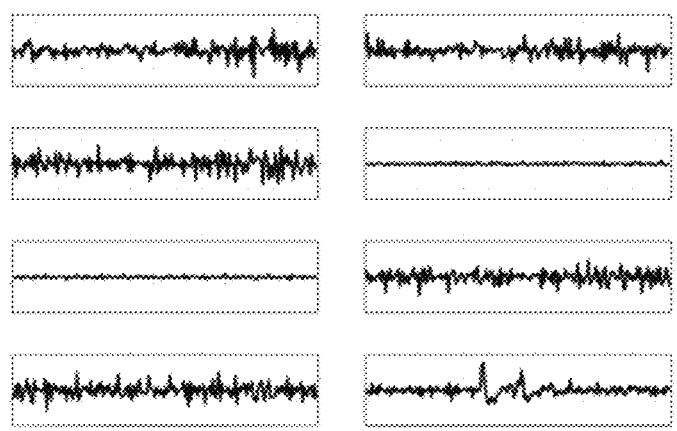

Qualitative patterns may easily be discerned in multiple data streams obtained simultaneously from a muscle group required to perform a specific movement. This is illustrated in FIG. 1 showing the EMGs for: (a) of a relaxed hand, (b) hand outward and (c) hand inward. As can be appreciated, there are different average signal intensities among the eight EMGs of the sensors acquired from two different hand positions.

However, a quantitative analysis helps determining the degree of pattern similarity between the EMGs of a healthy subject and an injured subject attempting to make the same motion. Several known detection and classification algorithms have been applied to EMG data in the past. These algorithms include single-threshold, double-threshold and decomposition analysis such as the techniques explained by Reaz et al, *Techniques of EMG signal analysis: detection, processing, classification and applications*, Biol. Proced. Online 2006; 8(1): 11-35, incorporated by reference herein in its entirety.

For example, paired and unpaired student T-tests can be used when measuring the similarity of multiple EMG patterns using integrated EMG average, single-threshold or double-threshold analysis. For an initial evaluation, a t score of $p=0.2$ can serve as an acceptable quantitative criterion where there is an 80 percent similarity between the EMG patterns between the healthy and injured subjects.

More advanced analytical algorithms may be used, such as decomposition analysis, that uses wavelet analysis and principal components analysis of wavelet coefficients that are well suited for EMG data analysis and can be very advantageous in measuring similarities in EMG.

These analytical algorithms can also provide important information with regard to the response of specific muscles of the injured subject that may not appear similar to the healthy subject.

The most direct method to determine if the healthy subject and the injured subject have a practical degree of similarity is to test the retraining system, that has been calibrated by the healthy subject, on the injured subject to confirm if the desired movement is obtained.

Therefore, any quantitative and/or qualitative method can be used alone or in combination as long as a statistically significant match is achieved for acceptable use of the apparatus by the injured subject.

The Therapy

According to a preferred embodiment of the invention, the first phase of therapy is conducted by placing the apparatus $5b$ on the injured subject while the healthy subject wears the EM sensors $5a$. Now, when the healthy subject performs the calibrated motion or motions, the apparatus $5b$ moves the body parts or limbs of the injured subject in the same manner and direction as the healthy subject moves his/her body parts or limbs. This aspect of the therapy provides direct visualization for the injured subject who will see both the motion of the healthy subject's body parts or limbs, as well as, his/her own body parts or limbs performing the same motions. In addition, this helps stimulate some physical muscle memory sensation of the desired motion for the injured subject.

As part of the next phase of therapy, the injured subject wears both the EM sensors $5a$ proximal to the neuromuscular injury and the apparatus $5b$ on the injured subject distal to the neuromuscular injury. Note that the position of the EM sensors $5a$ on the injured subject must be substantially the same position where the EM sensors $5a$ were placed on the healthy subject in order to maintain the similarity between the EMGs (i.e., the muscular movement) of the healthy subject and the injured subject attempting to make the same motion.

When the injured subject attempts to perform the calibrated movement, the computer will detect the injured subject's validated set of electromyo impulses and activate the mechanical servo motors to control the support elements of the apparatus so that the body parts move in the expected directions with the expected motion.

Therapy Methodology

A. EMG Evaluation of the Injury
1. The EM sensor is placed on the injured subject proximal to the location of the injury.
2. The EMG of the injured subject are obtained when the injured subject attempts specific motions while the EM sensor is placed at different locations along the neural pathway proximal to the injury starting at the position furthest from the injury.
3. The locus of the EM injury is mapped by evaluating the EMGs at the different positions proximal to the injury to determine where the EMG no longer significantly matches the EMG from healthy subjects.
4. Evaluate the electromyograph (EMG) data to determine the optimal EM sensor position that produces the maximum intensity and the highest degree of matching with EMGs from healthy subjects performing the same specific motions.
5. Evaluate the injured subject's EMGs with those from the healthy subject to ensure their EM signals significantly match those of the injured subject to serve as the secondary source of the EM impulses during the initial phase of therapy.

B. Calibration and Validation of the System
1. The EM sensor are placed on the healthy subject at substantially the same position previously determined to obtain the optimal EM signals from the injured subject.
2. The system is calibrated by having the healthy subject make specific motions and recording the EM signals by the microcomputer, as previously explained.
3. The apparatus is placed on the injured subject, wherein the apparatus is connected to the EM sensor via wire or wirelessly.
4. The healthy subject performs the recorded motion and the apparatus is evaluated to ensure that the same motion is performed on the injured subject.

C. Therapy Regime and Evaluation

Phase I
1. An EM sensor is placed on a healthy subject.
2. The apparatus is placed on an injured subject.
3. A second EM sensor is placed on the injured subject, wherein the second EM sensor is not connected to the apparatus.
4. The healthy subject performs the desired moment.
5. The injured subject experiences the same movement being performed by the healthy subject and this is confirmed visually and tactilely.
6. The EMGs from the healthy subject and injured subject are evaluated for the similarity and to determine the progress of therapy.

Phase II
1. The System (EM sensor and apparatus) is placed on the injured subject.
2. The injured subject attempts to perform the desired moment.
3. The EMG of the injured subject, as well as, the motion of the apparatus in the injured subject are evaluated with respect to the healthy subject.
4. At the end of the therapy session, the system is removed from the injured subject who then attempts to perform the desired motion without the aid of the system.
5. The progress of the retraining is evaluated.

One important aspect of the present invention is that the healthy subject can be the therapist who directly controls the activity of the injured subject during the first phase of the therapy. However, if the correlation of EMGs between the therapist (healthy subject) and the injured subject is not adequate, another healthy subject such as a family member having EM signals that better match the injured subject can be used. According to another embodiment of the invention, if the correlation between the EMGs of the healthy subject and the injured subject is not adequate, the computer can be programmed to consider the inadequate injured subject's set of EM signals as being significantly equivalent to the set EM signals of the healthy subject. This is done based on the assumption that the injured subject is intending to perform the same motion that the healthy subject performed even though the injured subject's set of EM signals might not be adequate or unexpected. Of course, this assumption must be validated by visually ensuring that the apparatus moves as expected when controlled by the injured subject's EM signals detected by EM sensor worn by the injured subject.

Another important aspect of the invention is that the system can be used in a group session format where the therapist acts as the healthy EM source for a group of subjects with similar injuries each wearing an apparatus 5b paired with the EM sensor 5a of the therapist. The same evaluation, calibration and validation steps should be individually performed on every injured subject.

EXAMPLES

Specific embodiments of the invention will be explained in relation to injuries that affects the motion of the elbow, wrist and hand. However, the application of the invention is not limited to these joints and may be applied to other neural muscular injuries alone or in groups.

Example 1—a System to Retrain Flexing Motion

An injured subject has lost the function of moving his/her wrist which can be retrained with the retraining system comprising the operational components previously described. In this example, the single function of moving or bending the hand inward and outward at the wrist relative to the body is desired. As shown in FIG. 4, the system requires two servo motors 4 to control the support element of the hand 2c that moves or bends the wrist joint and accomplishes the desired motion. It is also envisioned that at least one servo motor with the necessary capacity can be used to move the support element. For this function an electromyo armband 5 is place on the upper forearm distal to the elbow and connected to the microcomputer 3 via a wireless connection.

Figure 5:
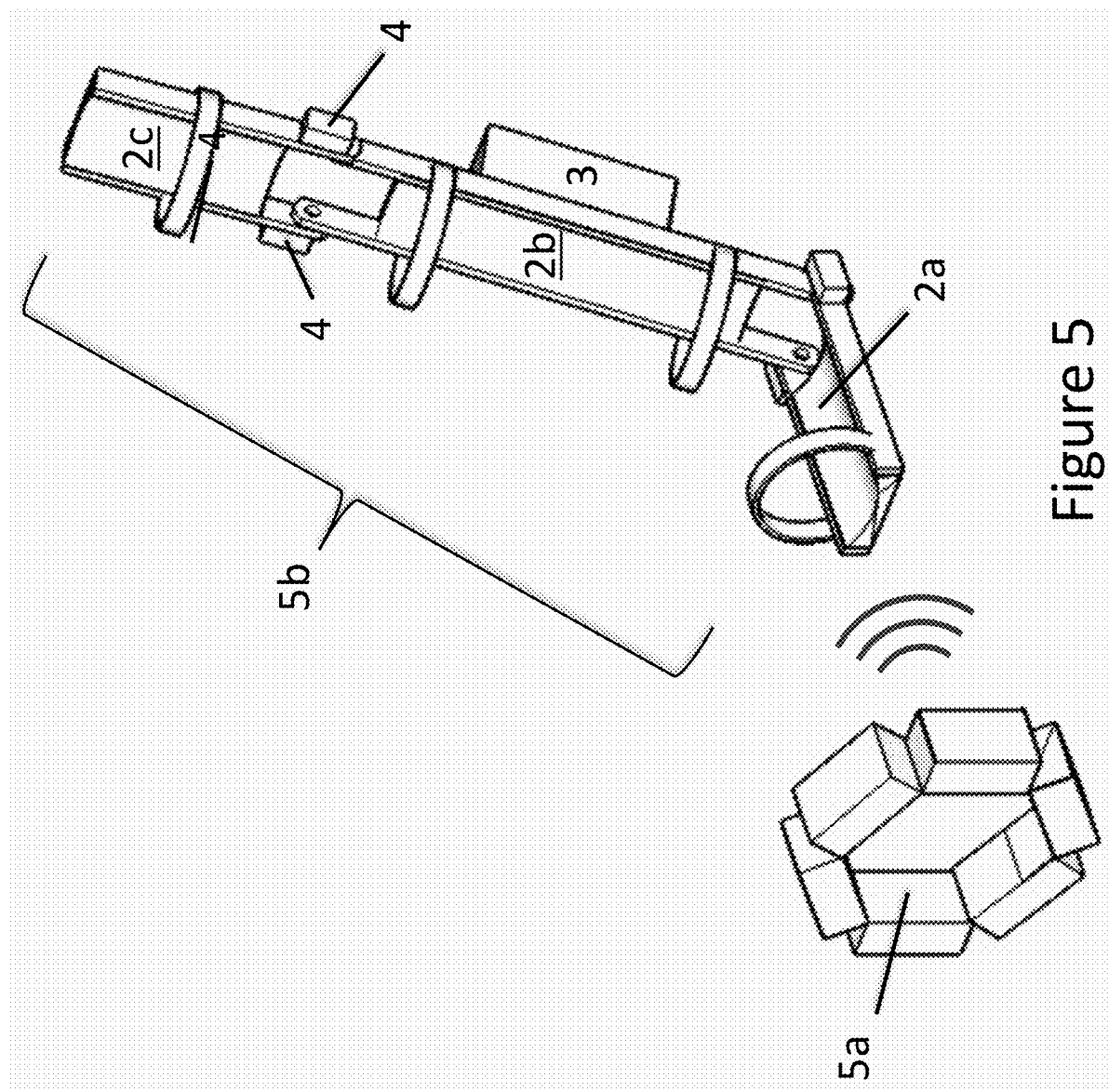
FIG. 5 shows an embodiment of the therapeutic system for an elbow with the forearm in the inward position, according to the invention.
Figure 6A:
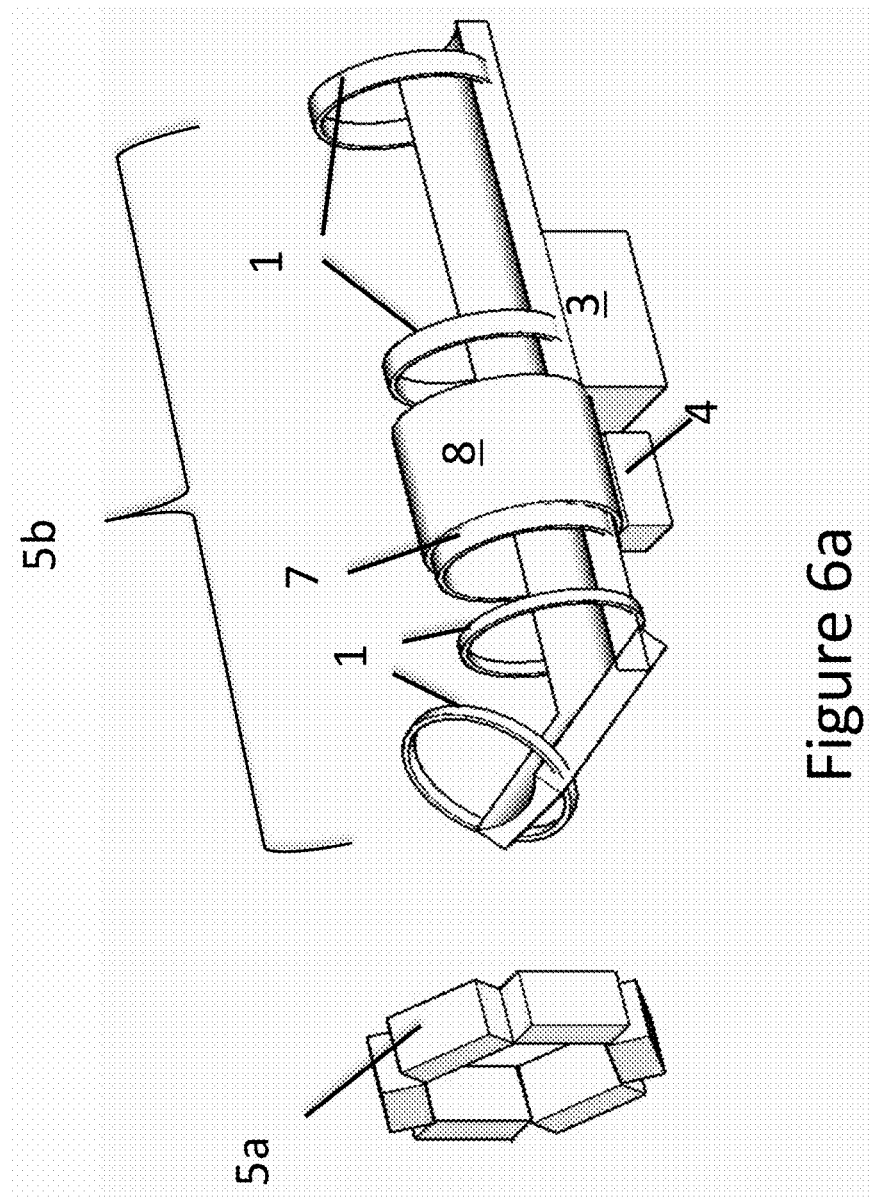
FIG. 6a shows an embodiment of the therapeutic system for the rotation of an arm, according to the invention.

An injured subject has lost the function of moving his/her elbow. FIG. 5 illustrates an embodiment of a system to perform the motion necessary to bend the elbow such that the forearm is moved to an inward position towards the upper arm. The electromyo armband 5 needs to be worn on the upper arm proximal to the injury and connected to the microcomputer 3 via a wireless connection.

Example 2—a System to Retrain Rotational Motion

For rotation of the forearm and hand from the elbow, a rotary joint arrangement and a geared servo motor are required. The rotary joint arrangement is comprised of two cylinders where an inner fixed cylinder 7 is attached to the proximal section of the forearm support element and an outer rotational cylinder 8 is attached to the distal section of the forearm support element. The geared servo motor 4 is mounted on the outer rotational cylinder 8 to cause the outer rotational cylinder 8 and the distal section of the forearm support element to rotate independently from the fixed proximal section of the forearm support element. The microcomputer 3 is preferably mounted on the distal forearm support element, as illustrated in FIGS. 6a-6d.

Of course, the control parameters of the geared servo motor 4 are selected and controlled as previously explained in order to achieve the desired rotation of the outer rotational cylinder 8.

As can be appreciated, the system can also be used on other body parts that normally require a degree of rotation such as but not limited to a neck, legs and a torso. In addition, an apparatus according to the present invention can combine the motors, supporting elements and/or rotary joint arrangement necessary to move and/or train a body part that combines bending and rotating motions. This solution can be provided as a single integral apparatus or as separate apparatus that are coupled to and controlled by at least one EM sensor. In doing so, one apparatus can be controlled by a first EM sensor while another apparatus can be controlled by a second EM sensor.

It is also envisioned that a single apparatus can include more than one microcomputer 3 so that at least a set of supporting elements and/or rotary joint arrangement can be controlled by a first microcomputer which is coupled to a first EM sensor and at least another set of supporting elements and/or rotary joint arrangement can be controlled by a second microcomputer which is coupled to a second EM sensor.

Example 3—The Therapy

The microcomputer calibration data is acquired from a healthy subject wearing the EM sensing armband Sa. The microcomputer records the EM impulses from the armband 5a while the healthy subject performs the desired training motions.

The electromyo impulses are then acquired from the injured subject attempting to perform the same set of motions while wearing the armband 5a in the same position where the armband 5a was placed on the healthy subject. The two sets of data are then compared to determine if the data are statistically equivalent. This validates that the injured subject has the capacity to generate muscular impulses that the computer 3 can recognize and control the retraining apparatus 5b to perform the desired motions.

Next, the apparatus 5b is secured to the injured subject (for example with hook and loop bands 1) while the electromyo armband Sa is worn on the healthy subject. When the healthy subject performs the desired motion, the apparatus 5b moves the injured subject's body part or limb in the same manner. This validates that the apparatus 5b is properly paired with the electromyo armband Sa and functions on an injured subject as expected. This also provides both visual and tactile sensations for the injured subject.

Now, when the injured subject is fitted with both the electromyo armband Sa and the apparatus 5b, and the injured subject attempts to perform the desired motion, the computer 3 will recognize the recorded muscular impulses for the specific motion and activate the servo motors 4 to move the support elements (2a-2e) in the expected motion.

Example 4—A Complex Therapy System to Retrain Multiple Motions

An injury to the nerves and muscles below the upper arm involving the elbow, wrist, hand and fingers is highly complex. This would require not only the combination of components of the apparatuses illustrated in FIGS. 4-6d, but also activated support elements attached to each finger of the hand. At first, each desired motion of the elbow, wrist and finger joint would need to be retrained individually, then in simple combinations among them, before normal complex motions could be performed. The controlled progression of these therapy steps would be programmed into the microcomputer 3 after the full range of motions was calibrated using healthy subjects, according to the inventive method of the invention. This computerized progression would provide incremental progress for the injured subject and objective guidance to the therapist in order to evaluate and determine when the subject is ready for the next step in the retraining process.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

We claim:

1. A method for validating a retraining system configured to be used on an injured subject, said method comprising:
obtaining from an electromyo (EM) sensor a set of electromyograph (EMG) data when an injured subject attempts to perform a specific motion of an injured body part while the EM sensor is placed at different locations along a neural pathway proximal to an injury starting at a position furthest from the injury;
evaluating said set of electromyograph (EMG) data to determine an EM sensor position on the injured subject that produces a maximum EMG average intensity data;
comparing said maximum EMG average intensity data of the injured subject with EMG data from a healthy subject that corresponds to the same specific motion of the same body part on said healthy subject to determine if said maximum EMG average intensity data and said EMG data from the healthy subject are significantly matched; and
validating that the injured subject is able to control movement of a retraining apparatus of the retraining system if said maximum EMG average intensity data of the injured subject and said EMG data from the healthy subject are significantly matched.

2. The method of claim 1, wherein said retraining system comprises a processing module that allows the injured subject to control the movement of said retraining apparatus when said maximum EMG average intensity data of the injured subject and said EMG data from the healthy subject are significantly matched.

3. The method of claim 1, wherein said retraining system comprises a processing module that allows the injured subject to control the movement of said retraining apparatus if said maximum EMG average intensity data of the injured subject and said EMG data from the healthy subject are not significantly matched.

4. The method of claim 3, wherein said processing module is instructed to consider the mismatch between the maximum EMG average intensity data of the injured subject and said EMG data from the healthy subject as being a significant match in order to allow the injured subject to control the movement of said retraining apparatus.

5. A method for controlling a retraining system configured to be used on an injured subject, the method comprising:
placing an electromyo (EM) sensor at a position on a healthy body part of a healthy subject, wherein said position is the same position as a position where another electromyo (EM) sensor was placed on an injured body part of an injured subject that was previously determined to generate specific electromyograph (EMG) signals from the injured subject;
placing a retraining apparatus on the injured body part of said injured subject, wherein said retraining apparatus is connected to the EM sensor;
having the healthy subject move the healthy body part in a specific motion in order to generate first EM signals that are associated to said specific motion which are sensed by the EM sensor; and
controlling movement of said retraining apparatus based on the first EM signals sensed by said EM sensor so that the retraining apparatus replicates said specific motion on said injured body part of the injured subject.

6. The method of claim 5, further comprising having said another EM sensor generating the specific electromyograph (EMG) signals, said another EM sensor is not connected to the retraining apparatus; and
comparing said first EMG signals from the healthy subject with said specific electromyograph (EMG) signals from the injured subject to evaluate a progress of a retraining therapy.

7. The method of claim 5, further comprising placing another retraining apparatus on the same injured body part of a second injured subject, wherein said second retraining apparatus is connected to the EM sensor; and controlling movement of said retraining apparatus and said another retraining apparatus based on the first EM signals sensed by said EM sensor so that the retraining apparatus and said another retraining apparatus replicate said specific motion on the injured body part of the injured subject and the second injured subject.

8. The method of claim 7, wherein said retraining apparatus and said another retraining apparatus are controlled to be moved in synchrony, sequentially, at different times or at random.

9. The method of claim 5, wherein said retraining apparatus and said another retraining apparatus comprise each at least one support element and at least one motor coupled to said at least one support element.

10. The method of claim 9, wherein said at least one motor rotates said at least one support element which rotates said injured body part.

11. The method of claim 9, wherein said at least one motor moves said at least one support element which bends said injured body part.

12. The method of claim 5, wherein the electromyo (EM) sensor and the another electromyo (EM) sensor comprise each a plurality of sensing elements.

13. A method for controlling a retraining system configured to be used on an injured subject, the method comprising:
placing an electromyo (EM) sensor and a retraining apparatus on an injured subject, wherein said retraining apparatus have been previously configured to perform specific movements based on first electromyograph (EMG) signals generated by movement of a healthy body part of a healthy subject;
having the injured subject performed said specific movement with an injured body part so that the EM sensor generates second EMG signals which are compared to said first EMG signals in order to control said retraining apparatus to assist movement of said injured body part by replicating said specific movement of the healthy body part based on the comparison between said first EMG signals and said second EMG signals.

14. The method of claim 13, wherein said retraining apparatus replicates said specific movement of the healthy body part when said comparison indicates that said first EMG signals and said second EMG signals are significantly matched.

15. The method of claim 13, further comprising evaluating the second EMG data of and the motion of the retraining apparatus to determine a progress of the retraining therapy.

16. The method of claim 13, further comprising removing said EM sensor and said retraining apparatus from the injured subject so that said injured subject attempts to perform the specific movement without the aid of the EM sensor and said retraining apparatus.

17. The method of claim 13, wherein the step of controlling said retraining apparatus to assist movement of said injured body part comprises actuating at least one motor mechanically coupled to at least one supporting element of said retraining apparatus, said at least one supporting element being coupled to the injured body part so that the at least one supporting element moves the injured body part.

18. A method for controlling a retraining system configured to be used on a plurality of injured subjects, the method comprising:
providing a first electromyo (EM) sensor on a healthy body part of a healthy subject;
providing a plurality of retraining apparatus on a plurality of injured subjects, wherein each retraining apparatus is coupled to an injured body part of each injured subject;
having the healthy subject move the healthy body part in a specific motion in order to generate first EM signals that are sensed by the first EM sensor; and
moving said plurality of retraining apparatus to replicate said specific motion on said injured body parts when the generated first EM signals correspond to a set of EM signals associated to said specific motion.

19. The method of claim 18, further comprising providing a plurality of second electromyo (EM) sensors on said plurality of injured subjects, wherein each second EM sensor is coupled to the injured body part of each injured subject so that each second EM sensor generates second EM signals that are compared to said first EM signals to determine a retraining progress of each injured subject of said plurality of injured subjects.

20. The method of claim 18, wherein the step of moving said plurality of retraining apparatus comprises actuating at least one motor mechanically coupled to at least one supporting element of provided on each of said retraining apparatus, said at least one supporting element being coupled to the injured body part so that each of the at least one supporting element moves a respective injured body part.

* * * * *